(12) United States Patent
Evers et al.

(10) Patent No.: US 6,503,084 B2
(45) Date of Patent: Jan. 7, 2003

(54) METHOD FOR DISPENSING DENTAL MATERIALS

(75) Inventors: Markus Evers, Constance (DE); Uwe Walz, Constance (DE); Andreas E. Grützner, Reichenau (DE); Joachim E. Klee, Radolfzell (DE)

(73) Assignee: Dentsply DeTrey G.m.b.H. (DE)

( * ) Notice: Subject to any disclaimer, the term of this patent is extended or adjusted under 35 U.S.C. 154(b) by 0 days.

(21) Appl. No.: 09/930,743

(22) Filed: Aug. 2, 2001

(65) Prior Publication Data

US 2002/0076671 A1 Jun. 20, 2002

Related U.S. Application Data

(63) Continuation-in-part of application No. 09/813,625, filed on Mar. 21, 2001, now abandoned, which is a continuation-in-part of application No. 09/737,048, filed on Dec. 14, 2000, now abandoned.
(60) Provisional application No. 60/185,214, filed on Feb. 24, 2000.

(51) Int. Cl.[7] .................................................. A61C 5/04
(52) U.S. Cl. ............................................. 433/226; 433/90
(58) Field of Search ........................... 433/89, 90, 226, 433/228.1; 222/386; 401/176

(56) References Cited

U.S. PATENT DOCUMENTS

| | | | |
|---|---|---|---|
| 4,296,094 A | 10/1981 | Matsushima et al. | 424/49 |
| 4,391,590 A | 7/1983 | Dougherty | 433/90 |
| 4,433,779 A | 2/1984 | Schmid Jr. et al. | 206/220 |
| 4,450,957 A | 5/1984 | Cohen | 206/220 |
| 4,569,662 A | 2/1986 | Dragan | 433/89 |
| 4,619,613 A | 10/1986 | Dragan | 433/90 |
| 4,765,984 A | 8/1988 | Vellekoop et al. | 424/441 |
| 4,767,326 A | 8/1988 | Bennett et al. | 433/90 |
| 4,963,093 A | 10/1990 | Dragan | 433/90 |
| 4,997,371 A | 3/1991 | Fischer | 433/90 |
| 5,026,283 A | 6/1991 | Osanai et al. | 433/90 |
| 5,052,927 A | 10/1991 | Discko, Jr. | 433/90 |
| 5,061,179 A | 10/1991 | Dragan | 433/90 |
| 5,083,921 A | 1/1992 | Dragan | 433/90 |
| 5,094,839 A | 3/1992 | Lowder et al. | 424/49 |
| 5,100,320 A | 3/1992 | Martin et al. | 433/90 |
| 5,122,057 A | 6/1992 | Discko, Jr. | 433/90 |

(List continued on next page.)

FOREIGN PATENT DOCUMENTS

| | | |
|---|---|---|
| DE | 4119522 | 5/1991 |
| DE | 9100497 | 5/1991 |
| DE | 4118336 | 12/1992 |
| EP | 848935 | 12/1996 |
| GB | 2193654 | 8/1987 |
| GB | 2251385 | 12/1991 |
| WO | 95/06443 | 3/1995 |
| WO | 98/00071 | 1/1998 |
| WO | 00/44300 | 8/2000 |

Primary Examiner—Todd E. Manahan
(74) Attorney, Agent, or Firm—Dale R. Lovercheck; James B. Bieber

(57) ABSTRACT

A method of venting during sealing the cartridge. The cartridge body has an external wall, a generally cylindrical internal chamber wall having an internal chamber wall diameter and enclosing a cartridge chamber, and at least one channel wall forming a channel (or groove) in the chamber wall. The piston has a generally cylindrical plug wall positioned adjacent to the generally cylindrical internal chamber wall. The cylindrical plug wall has a diameter substantially equal to the diameter of the cylindrical internal chamber wall. Dental material is conveyed into the cartridge chamber. The piston is pressed into the cartridge chamber while venting gas from the cartridge chamber through the channel prior to forming a hermetic seal around the dental material in the cartridge chamber.

13 Claims, 5 Drawing Sheets

U.S. PATENT DOCUMENTS

| | | | |
|---|---|---|---|
| 5,129,825 A | 7/1992 | Discko, Jr. | 433/90 |
| 5,172,807 A | 12/1992 | Dragan et al. | 206/219 |
| 5,267,859 A | 12/1993 | Discko, Jr. | 433/89 |
| 5,286,257 A | 2/1994 | Fischer | 604/82 |
| 5,324,273 A | 6/1994 | Discko, Jr. | 604/240 |
| 5,336,088 A | 8/1994 | Discko, Jr. | 433/90 |
| 5,348,154 A | 9/1994 | Jacobs et al. | 206/369 |
| 5,350,059 A | 9/1994 | Chester et al. | 206/63 |
| 5,445,523 A | 8/1995 | Fischer et al. | 433/90 |
| 5,460,523 A | 10/1995 | Schulman | 433/90 |
| 5,525,647 A | 6/1996 | Eichmiller | 523/105 |
| 5,697,918 A | 12/1997 | Fischer | 604/227 |
| 5,707,234 A | 1/1998 | Bender | 433/90 |
| 5,770,182 A | 6/1998 | Fischer | 424/49 |
| 5,848,894 A | 12/1998 | Rogers | 433/90 |
| 5,851,512 A | 12/1998 | Fischer | 424/49 |
| 5,855,870 A | 1/1999 | Fischer | 424/49 |
| 5,871,355 A | 2/1999 | Dragan et al. | 433/90 |
| 5,938,439 A | 8/1999 | Martins et al. | 433/90 |
| 6,099,307 A * | 8/2000 | Discko, Jr. | 433/90 |
| 6,135,771 A * | 10/2000 | Dragan et al. | 433/90 |

*Primary Examiner—*

METHOD FOR DISPENSING DENTAL MATERIALS

This is a continuation-in-part of patent application Ser. No. 09/813,625 filed Mar. 21, 2001 now abandonded which is a continuation-in-part of patent application Ser. No. 09/737,048 filed Dec. 14, 2000, now abandonded which claims the benefit of U.S. Provisional patent application No. 60/185,214 filed Feb. 24, 2000.

The invention relates to plugged dispenser cartridges for viscous dental materials. The invention provides improved plugged dental dispenser cartridges having at least one channel (passage or groove), which allows air to pass out of the chamber as it is filled with compressed viscous dental materials during plugging. This provides a plugged cartridge chamber filled with compressed viscous dental materials having low internal gauge pressure. The gauge pressure within the plugged cartridge chamber is lower than in prior art plugged cartridge chambers filled with viscous dental material. Beneficially, the invention provides less internal gauge pressure within the plugged cartridge chamber. A cap fits onto a needle cannula in fluid flow communication with the plugged cartridge chamber. Prior art plugged cartridges spontaneously extrude viscous dental material through the needle cannula causing cap loss during storage and transport of the plugged cartridge. Because there is less internal gauge pressure within the plugged cartridge chamber of the invention, such spontaneous extrusion and cap loss are effectively avoided.

BACKGROUND OF INVENTION

Petrich et al in WO 00/44300 disclose a cartridge which at most is half filled with a high viscosity dental composition. The cartridge has a stepped chamber (26, 28) and a piston with two cylindrical portions (36 and 40) on a shank (38) for high viscosity dental compositions, such as restoratives, adhesives, cements etching gels, and sealants as see page 1 lines 30–32 and pages 5 and 6. The stepped chamber cartridge with two cylindrical pistons of Petrich et al requires a shank and first chamber which are about as long as the second chamber. The present invention overcomes the problems of the prior art by providing a cartridge almost entirely filled with a high viscosity dental composition in a single chamber with a single diameter, and has a single piston with a single outer diameter (and no shank).

During filling of prior art plugged cartridges with viscous dental restorative materials there is significant compression of air and viscous dental restorative materials. The compressed air is incorporated into the viscous dental material during filling. During subsequent storage of prior art plugged cartridges there is spontaneous extrusion of viscous dental material. Thus, during placement of a displaceable piston, compression of air takes place followed by partial extrusion of material. The sealed cartridges have substantial gauge pressure. During storage and transport of the plugged cartridge this results in cartridges breaking, and spontaneously extrusion of viscous dental material through the needle cannula causing cap loss. These problems of the prior art are overcome by the present invention. In the present invention air passes out of the cartridge through grooves in the chamber wall during placement of a displaceable piston. Because there is less internal gauge pressure within the plugged cartridge chamber of the invention, cartridge breakage, spontaneous extrusion and cap loss are effectively avoided. The invention provides controlled application of flowable or gel-form materials or medicinal products. Force applied to the cartridge body during extrusion is reduced by reducing the amount of air entrapped in the cartridge. This reduces the cartridge body internal gauge pressure. So when force is applied to the plug to extrude the composition, the total force on the cartridge body is less than in prior cartridges.

SUMMARY OF THE INVENTION

A dental cartridge chamber is filled with a high viscosity dental composition and a piston is pressed into the chamber. The piston has a generally cylindrical piston wall, an inner face and an outer face. The cartridge has a generally cylindrical chamber wall having at least one groove. Dental material is conveyed into the cartridge chamber. The cylindrical chamber wall encloses the dental composition and air. The air passes through the groove while the piston is pressed into the chamber. Pressing the piston causes it to move into the chamber. The outer face of the piston presses the high viscosity dental composition, as the cylindrical piston wall is guided along the cylindrical chamber wall. The chamber wall has at least one groove adjacent to the opening for the plug. The groove channel is open to the cartridge chamber. The groove channel extends through the external wall. As the plug is pressed into the cartridge chamber air passes from a cartridge chamber through the groove in a chamber wall. Thus, the piston is pressed into the cartridge chamber while gas passes from the cartridge chamber through the groove channel prior to hermetically sealing dental material in the cartridge chamber. The cartridge also has a discharge nozzle, a needle cannula and a cap. The needle cannula allows direct, precise and hygienic placement of dental materials and provides a dentist with visibility of material during application to a tooth.

DETAILED DESCRIPTION OF THE INVENTION

Figure 1:
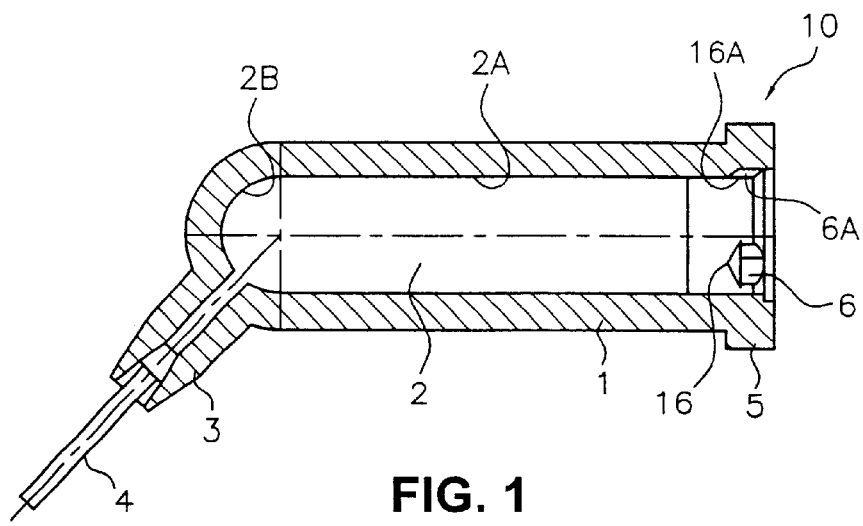
FIG. 1 is a cross-sectional side view of a cartridge with a needle cannula in accordance with the invention.
Figure 2:
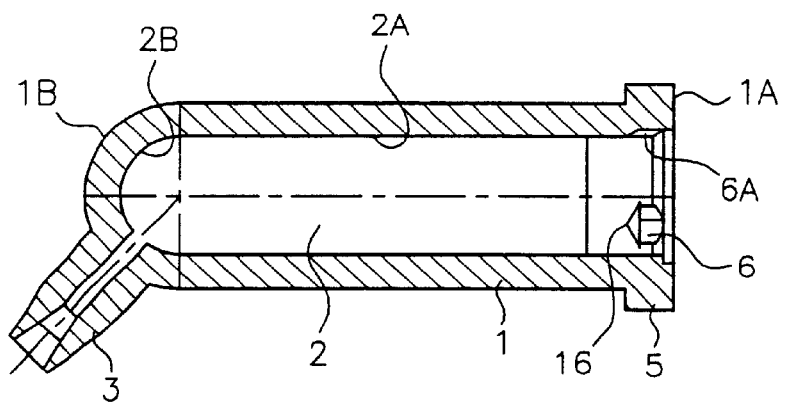
FIG. 2 is a cross-sectional side view of the cartridge shown in FIG. 1 but without a needle cannula.
Figure 3:
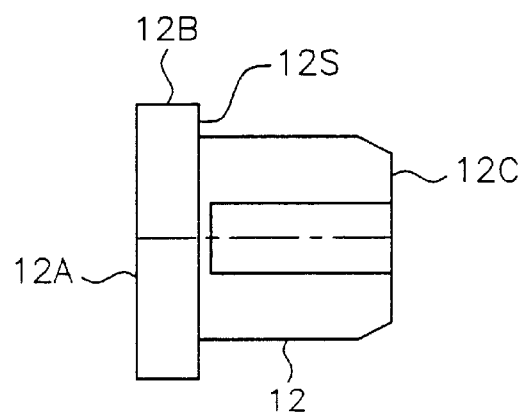
FIG. 3 is a cross-sectional side view of a piston for use with the cartridge shown in FIG. 1.
Figure 4:
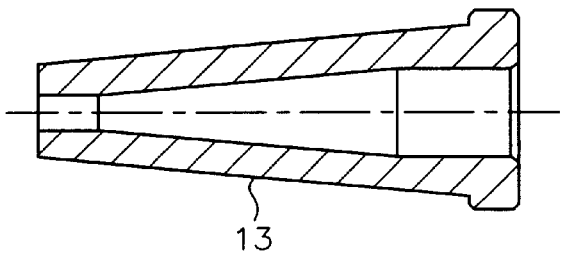
FIG. 4 is a cross-sectional side view of a cap for use with the cartridge shown in FIG. 1.
Figure 5:
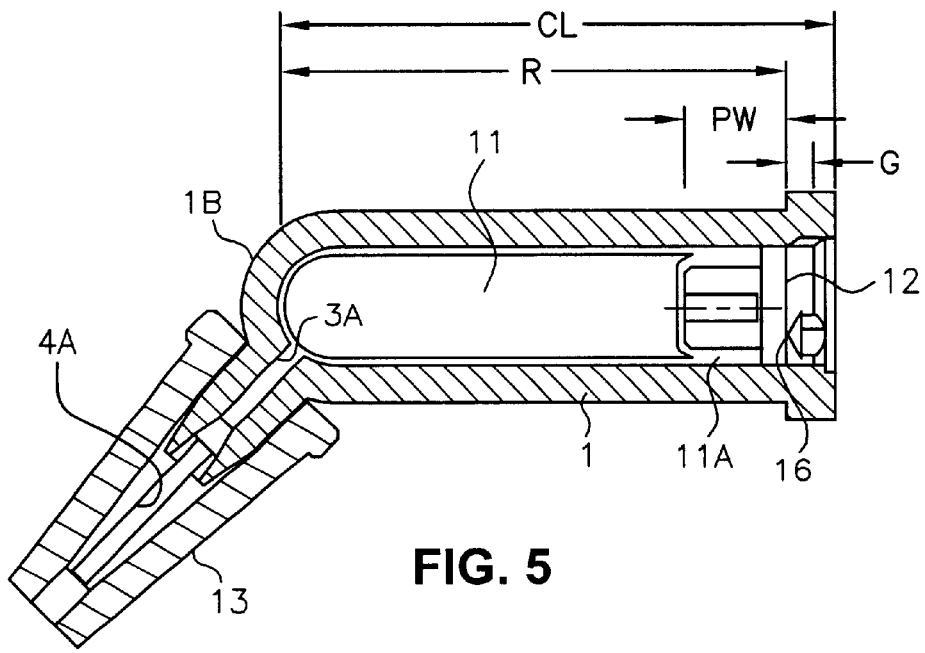
FIG. 5 is a cross-sectional side view of the cartridge shown in FIG. 1 with piston, needle and cap.
Figure 6:
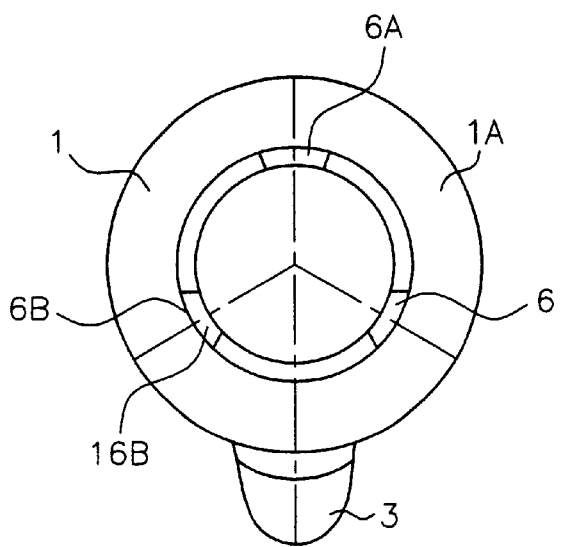
FIG. 6 is an end view of the cartridge as shown in FIG. 5.
Figure 7:
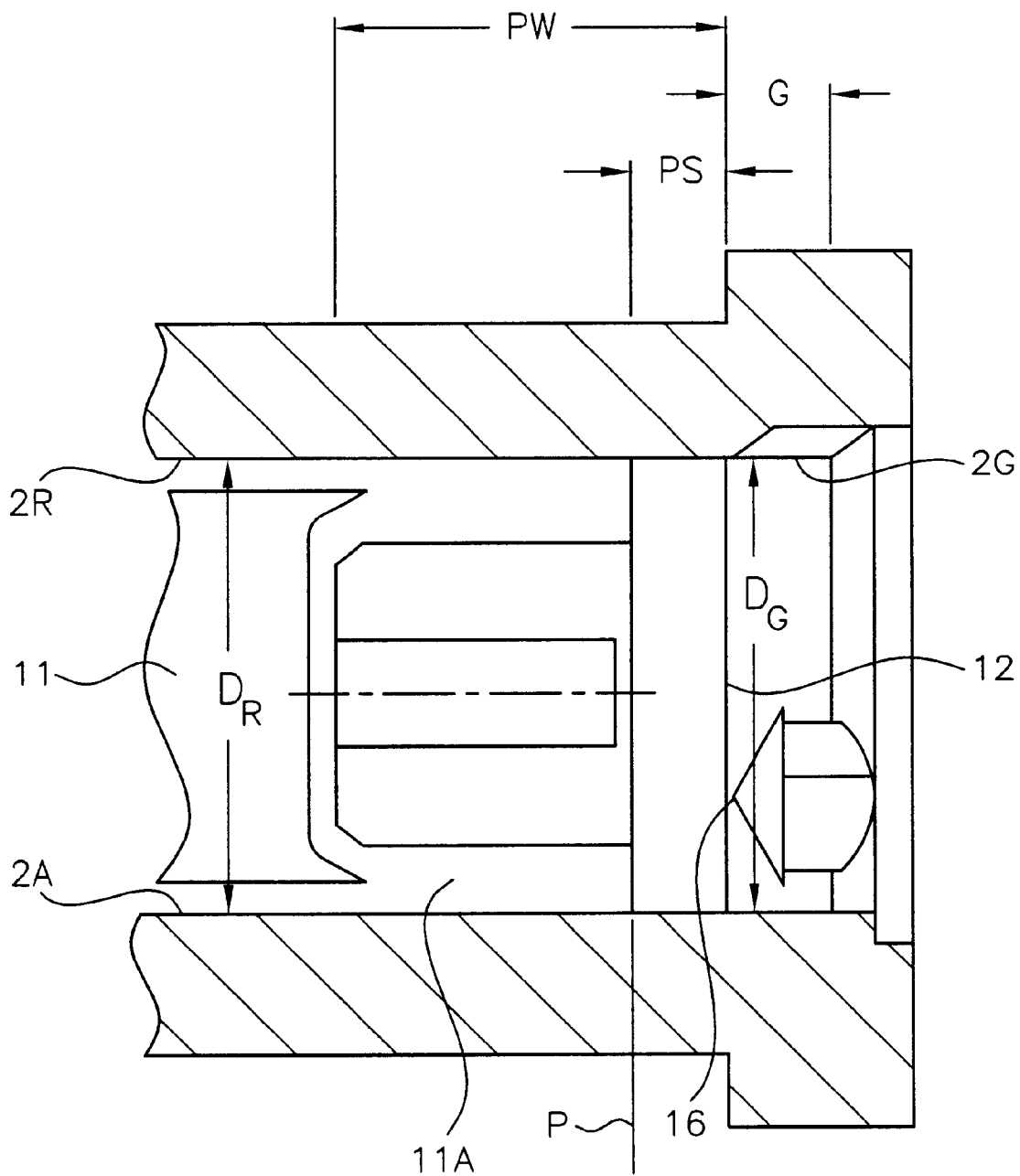
FIG. 7 is a partial cross-sectional side view of the cartridge shown in FIG. 1 with piston, needle and cap.
Figure 7A:
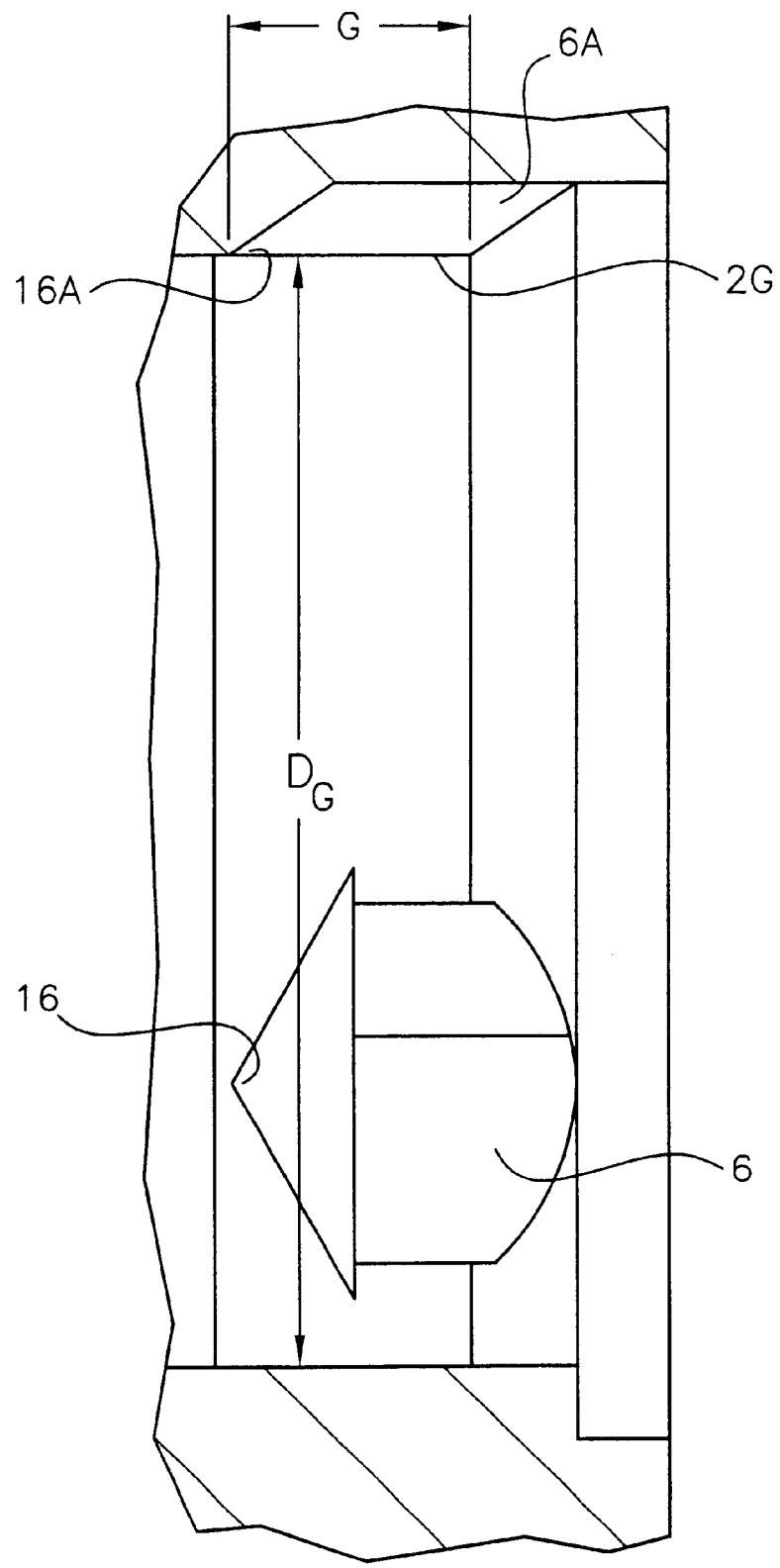
FIG. 7A is an enlarged portion of the partial cross-sectional side view of the cartridge shown in FIG. 7.
Figure 8:
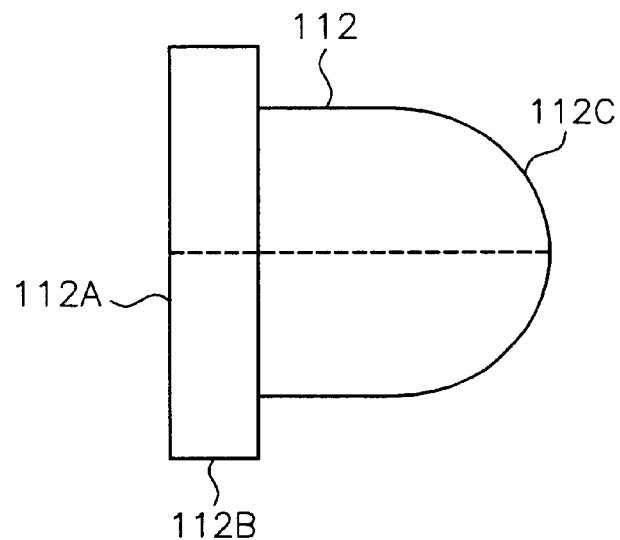
FIG. 8 is a cross-sectional side view of a piston for use with the cartridges shown in FIGS. 1, 2, 5, 6, 7 and 9.

The invention is now described with more particular reference to FIGS. 1 through 7A. FIG. 1 shows a cartridge 10 for dental material. Cartridge 10 is preferably used for direct application of dental material 11 to tooth tissue. Dental material 11 is preferably has from low to medium viscosity. Cartridge 10 includes a plastic body 1 having a generally cylindrical inner wall 2A enclosing a chamber having a reservoir portion 2 containing a predetermined amount of dental material 11. Typically, the amount of dental material 11 is from 0.01 to 1.0 ml. Plastic body 1 has annular end wall 1A, and hemispherical front end 1B having discharge nozzle 3. Nozzle channel wall 3A encloses a passageway extending from the chamber enclosed by wall 2A to a passageway enclosed by cannula passageway wall 4A extending through needle cannula 4 to the adjacent surroundings.

The cylindrical wall 2A has an opening at one end which is co-extensive to the cylindrical shape. The body portion has a hemispherical front end disposed in axial alignment with the axis of the body portion. A discharge nozzle 3 is angularly disposed to the hemispherical front end wall 2B, comprising a needle cannula 4 that is incorporated by a press fit, wherein the inner diameter of the discharge nozzle is smaller compared to the outer diameter of the needle cannula. The needle cannula 4 is preferably made of metal or rigid plastic material. A flange 5 extends outwardly about the open end of the body 1. A series of longitudinal extending channels 6, 6A and 6B in the region of the opened end of the body are circumferentially spaced about the internal surface of the body. A displaceable piston 12 seals the open end of the reservoir portion. Displaceable piston 12 has outer piston face 12A, cylindrical piston wall 12B and inner piston face 12C. Displaceable piston 12 has piston width PW. Outer piston face 12A has piston sealing width PS.

A cap 13 seals the discharge nozzle and needle cannula. The longitudinal extending channels of the cartridge allow air to exit the cartridge during filling. Plastic body 1, displaceable piston 12 and cap 13, are preferably made by injection molding of plastic (polymeric) materials.

Dental cartridge 10 has a generally cylindrical chamber wall having groove walls 6, 6A and 6B. The cylindrical chamber wall 2A encloses a dental composition 11 and air 11A. The piston is pressed into the cartridge chamber while gas passes from the cartridge chamber through the groove walls 6, 6A and 6B to the atmosphere outside of the cartridge. Thus, the air 11A passes through grooves formed by groove walls 6, 6A and 6B, while outer piston face 12A is pressed, and cylindrical piston wall 12B is guided by and along cylindrical chamber wall 2A.

Groove walls 6, 6A and 6B have inner ends 16, 16A and 16B. In storage position dental composition 11 is hermetically sealed within reservoir portion 2 of chamber wall 2A, and inner piston face 12C is positioned on the hemispherical front end wall 2B side, past the groove inner ends 16, 16A and 16B. Preferably, dental composition 11 is stored storage position within dental cartridge 10 for at least one week, more preferably for at least one month and most preferably for at least 6 months.

In use, force is applied to piston 12 and some of dental composition 11 is pushed by piston 12 from reservoir portion 2 into and through needle cannula 4 onto dental tissue in a patient's mouth. As some of dental composition 11 is pushed from reservoir portion 2, inner piston face 12C is moved toward the hemispherical front end wall 2B. Some of dental composition 11 may remain hermetically sealed in reservoir portion 2 of dental cartridge 10 for later use on the same or a different patient.

Direct, precise and hygienic placement of dental materials and unobstructed sight during use, are provided by a needle cannula 4, which is incorporated into the plastic body 1. The needle cannula 4 is made of a non-corrosive material. Most preferably the needle cannula 4 is made of stainless steel if it is used for example for the application of pit and fissure sealants or other flowable materials. The needle cannula is of flexible material for intraoral applications and root canal treatment.

Cartridge 10 allows a dentist to view application of material to tooth tissue. Needle cannula 4 permit direct and precise placement of dental materials to small cavities and orifices. This is particularly useful for pit and fissure sealing, root canal treatment, periodontal treatment, and for etching procedures. Cartridge 10 enables direct and hygienic placement of dental materials. Replacing needle cannula 4 between applications of dental material from a cartridge 10 to different patients avoids cross-contamination.

Passing air from the chamber during movement of the displaceable piston against the dental material 11 avoids pressure build-up within reservoir portion 2 of the chamber. Pressure build-up within reservoir portion 2 of the chamber can cause partial extrusion of material though the needle cannula 4. Preferably, a plurality of longitudinal extending channels, are circumferentially spaced in the region of the end and about the internal surface of plastic body portion. Venting air during placement of the displaceable piston avoids development of pressure during loading of material, which undesirably forces extrusion of material though needle cannula 4.

Plastic body portion 1 and displaceable piston 12 are fitted together such that their initial friction is minimized and a suitable extrusion force permits controlled application. Cap 13 fits the needle cannula such that undesired material extrusion is avoided during storage and transport.

Thus, dental cartridge 10, has piston 12 with piston width PW and piston outer wall 12B. Chamber wall 2A has a chamber wall length CL and at least one groove wall. The groove wall has a groove length G. Piston 12 is supported along the piston outer wall 12B by chamber wall 2A adjacent to the grooves 6, 6A and 6B. Chamber wall 2A at grooves 6, 6A and 6B has a grooved portion 2G with inner groove diameter $D_G$. Reservoir portion 2R of chamber wall 2A has reservoir diameter $D_R$. Inner groove diameter $D_G$ is effectively equal to reservoir diameter $D_R$ and piston outer wall diameter $D_P$. Because inner groove diameter $D_G$ is effectively equal to reservoir diameter $D_R$ and piston outer wall diameter $D_P$ of piston 12 contacts chamber wall 2A in the grooved portion 2G and in the reservoir portion 2R. As sealing piston face 12S moves from grooved portion 2G to reservoir portion 2R it hermetically seals dental material 11 within reservoir portion 2.

In sealed dental cartridge 10 chamber wall 2A has chamber wall length CL. Each of groove walls 6, 6A and 6B forms a groove channel with a groove inner end 16, 16A and 16B respectively. Each of groove walls 6, 6A and 6B has a groove length G. Piston 12 is supported along piston outer wall 12B by chamber wall 2A adjacent to the groove inner end. Dental composition 11 is sealed within reservoir portion 2R by piston sealing wall 12S. Reservoir portion 2R has reservoir length R. Reservoir length R is at least two times longer than groove length G.

Before sealing reservoir portion 2R plane P extends through groove portion 2G. As piston sealing wall 12S moves toward groove inner ends 16, 16A and 16B, air moves from reservoir portion 2R through the groove channel formed by groove walls 6, 6A and 6B and out of dental cartridge 10 into the ambient atmosphere.

During sealing of dental composition 11 within reservoir portion 2R, plane P on the face of piston sealing wall 12S moves from extending through groove portion 2G to extending through reservoir portion 2R. As the plane P moves from extending through groove portion 2G to extending through reservoir portion 2R piston sealing wall 12S hermetically seals reservoir portion 2R.

In sealed dental cartridge 10 chamber wall 2A has groove channels in groove portion 2G. The groove portion 2G has inner groove diameter $D_G$. Each groove channel has a groove inner end. Dental composition 11 is sealed within a reservoir portion 2R by piston sealing wall 12S. Reservoir portion 2R has reservoir diameter $D_R$. Reservoir diameter $D_R$ is effectively equal to inner groove diameter $D_G$.

The groove length G is less than 30 percent of the chamber wall length CL, and the piston width W is less than the groove length. The groove length G is less than 20 percent of the chamber wall length CL, and the length of piston width PW is less than 20 percent of length of the chamber wall length CL.

Dental composition 11 is hermetically sealed within reservoir portion 2R of chamber wall 2A. Reservoir portion 2R of chamber wall 2A has a reservoir length R. Reservoir length R is at least twice groove length G. Preferably reservoir length R is at least three times longer than groove length G. More preferably reservoir length R is at least four times longer than groove length G.

Inner piston face 12C is positioned on the side of hemispherical front end wall 2B. In sealed position sealing piston face 12S is past the inner ends of grooves 6 and 6A.

Figure 9:
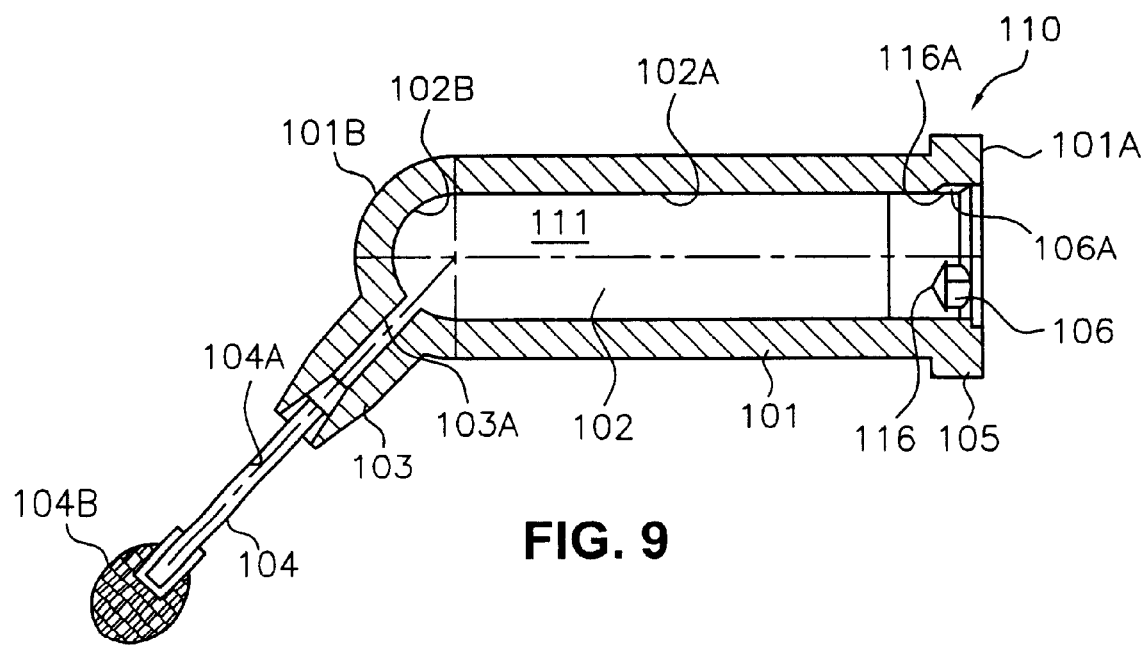
FIG. 9 is a cross-sectional side view of a cartridge having a needle cannula has a brush.

With more particular reference to FIG. 9 is seen cartridge 110 with a needle cannula 104 having a brush 104B. Plastic body 101 has annular end wall 101A, and hemispherical front end 101B having discharge nozzle 103. Nozzle channel wall 103A encloses a passageway extending from the chamber enclosed by wall 102A to a passageway enclosed by cannula passageway wall 104A extending through needle cannula 104 to the adjacent surroundings. When a brush is needed during application of dental composition 111 needle cannula 104 having a brush 104B is provided. A discharge nozzle 103 is angularly disposed to the hemispherical front end wall 102B, comprising needle cannula 104 that is incorporated by a press fit, wherein the inner diameter of the discharge nozzle is smaller compared to the outer diameter of the needle cannula. A flange 105 extends outwardly about the open end of the body 101.

Displaceable piston 112 has outer piston face 112A, cylindrical piston wall 112B and inner piston face 112C, which is hemispherical. Displaceable piston 112 may be used by insertion into the opening in annular end wall 101A of cartridge 101 or in cartridge 1 in place of displaceable piston 12.

Grooves 106 and 106A have inner ends 116 and 116A. In storage position dental composition 111 is hermetically sealed within reservoir portion 102 of chamber wall 102A, and inner piston face 112C is positioned on the hemispherical front end wall 102B side, past the inner ends of grooves 116 and 116A. Preferably, dental composition 111 is stored storage position within dental cartridge 110 for at least one week, more preferably for at least one month and most preferably for at least six months.

In use, force is applied to piston 112 and some of dental composition 111 is pushed by piston 112 from reservoir portion 102 into and through needle cannula 104 onto dental tissue in a patient's mouth. As some of dental composition 111 is pushed from reservoir portion 102, inner piston face 112C is moved toward the hemispherical front end wall 102B. Some of dental composition 111 may remain hermetically sealed in reservoir portion 102 of dental cartridge 110 for later use on the same or a different patient.

Preferably, the plastic body 1, displaceable piston 12 and cap 13 are composed of a plastic material such as polyethylene, polypropylene, polycarbonate, polyamide, polyacetal, polyester, polycycloolefins or copolymers thereof. The plastic body 1 and displaceable piston 12 are constructed of light transparent or light opaque material. They may be made of a material that is transparent to at least a portion of the visible light spectrum and opaque to the actinic light which would initiate polymerization of the dental materials. Plastic body 1, displaceable piston 12 and/or cap 13 may be colorcoded to indicate various kinds, weight or quantity of material 11 or to convey other information related of material 11.

In accordance with a preferred embodiment of the invention is provided a method of venting while sealing a cartridge. The cartridge body has an external wall, a generally cylindrical internal chamber wall enclosing a cartridge chamber, and at least one channel 6, 6A, 6B internal chamber wall. The channel is open to the cartridge chamber. The channel extends through the open end portion of the external wall. The piston 12 has a generally cylindrical plug wall positioned adjacent to the generally cylindrical internal chamber wall. The cylindrical plug wall has a diameter substantially equal to the diameter of the cylindrical internal chamber wall. Dental material is conveyed into the cartridge chamber. The piston is pressed into the cartridge internal chamber, wherein otherwise trapped gas is vented from the cartridge chamber through the channel prior to hermetically sealing dental material in the cartridge chamber.

Preferably, the piston has a dental material face and a plunger face, and the plunger face and the dental material face are in parallel planes, which intersect the cylindrical plug wall at an angle of 90 degrees. The channel in the chamber wall is not in fluid flow communication with the hermetically sealed chamber. The sealed chamber is substantially filled with dental material".

The cylindrical plug wall has a diameter substantially equal to the diameter of the cylindrical internal chamber wall, effectively forming a hermetically sealed chamber. The cartridge body wall 2A has at least one groove. Each groove is open to the cartridge chamber. Each groove extends through the external wall at the open end. The piston does not extend into either channel. the groove in the chamber wall is not in fluid flow communication with the hermetically sealed chamber.

The piston has a plunger face within the cartridge chamber. The cartridge body has a hemispherical end. The hemispherical end opens into a discharge nozzle. The discharge nozzle is in fluid flow communication with a needle cannula, and a cap seals the discharge nozzle and needle cannula.

The gauge pressure within reservoir portion 102 of chamber wall 102A is substantially the same before and after conveying dental material into it and hermetically sealing the dental material therein. The gauge pressure within reservoir portion 102 of chamber wall 102A before sealing is preferably within 1, 2 or 5 percent of the gauge pressure within reservoir portion 102 of chamber wall 102A after sealing.

The cartridge body has a hemispherical front end disposed in axial alignment with the axis of the body, and the discharge nozzle has a needle cannula which is press fit into the discharge nozzle passage. A cap seals the discharge nozzle and needle cannula. A flange extends outwardly at the open end of the body.

Gauge pressure as used herein refers to a pressure measured by a gauge, which reads zero pressure for ambient atmospheric pressure. Thus, positive gauge pressure readings are for pressures above atmospheric pressure, and negative gauge pressure readings are for pressures below atmospheric pressure. A difference in pressure between a pressure in a chamber and ambient atmospheric pressure outside of the chamber provides a positive gauge pressure reading when the pressure in the chamber is higher than ambient atmospheric pressure.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A dental method, comprising:
   providing a dental cartridge, comprising:
      a molded plastic cartridge body, a piston and 0.01 to 1.0 ml of a high viscosity dental composition,
      said piston having a piston sealing wall and a piston outer wall,
      said cartridge body having a hemispherical front end, a cylindrical portion, and a discharge nozzle,
      said cartridge body having a chamber wall having at least one groove wall forming a groove channel with a groove inner end, said groove wall having a groove length, said piston being supported along said piston outer wall by said chamber wall,
      said chamber wall having a reservoir portion,
      said high viscosity dental composition being sealed within a cartridge chamber enclosed by said reservoir portion and said piston sealing wall, when said piston sealing wall is in sealing position,
      said reservoir portion having a cylindrical section and a hemispherical end, said hemispherical end being integrally connected to and opening into said discharge nozzle, said cylindrical section having a reservoir axis, said discharge nozzle having a noble axis, said nozzle axis intersects said reservoir axis at an angular offset,
      said reservoir portion having a reservoir length,
      said reservoir length being at least two times longer than said groove length,
   moving said piston sealing wall toward said groove inner end while passing a substantial portion of air through said groove channel,
   conveying said high viscosity dental composition into said reservoir portion until said piston sealing wall is in sealing position and said cartridge chamber is effectively filled with at least 90 percent by volume of said high viscosity dental composition and at most 10 percent by volume of air,
   storing said dental cartridge for at least one week, and
   dispensing said high viscosity dental composition from said reservoir portion onto a dental tooth.

2. The method of claim 1 wherein said groove length is less than 15 percent of said reservoir length, and said cartridge body has a groove end having an outer flange.

3. The method of claim 1 wherein pressure within said cartridge chamber before said conveying is substantially equal to pressure within said cartridge chamber after said conveying.

4. The method of claim 1 wherein said high viscosity dental composition is polymerizable.

5. The method of claim 4 wherein said cartridge body and said piston are opaque to actinic light.

6. The method of claim 5 further comprising initiating polymerization of said high viscosity dental composition.

7. The method of claim 1 wherein said chamber wall has a nozzle end integrally connected to a discharge nozzle.

8. The method of claim 1 wherein said dental cartridge further comprises a canula, and said canula is supported by said nozzle and said high viscosity dental composition is polymerizable.

9. The method of claim 8 wherein said cartridge body and said piston are opaque to actinic light.

10. The method of claim 1 wherein said high viscosity dental composition is light curable and said molded plastic cartridge body, and said piston are opaque to actinic light.

11. The method of claim 1 wherein said dental cartridge further comprises a canula, and said canula is supported by said nozzle.

12. A dental method, comprising
    providing a dental cartridge, comprising:
       a molded plastic cartridge body, a piston and 0.01 to 1.0 ml of a high viscosity polymerizable dental composition,
       said piston having a piston sealing wall and a piston outer wall,
       said cartridge body having a hemispherical front end, a cylindrical portion, and a discharge nozzle,
       said cartridge body having a chamber wall having at least one groove wall forming a groove channel with a groove inner end, said groove wall having a groove length, said piston being supported along said piston outer wall by said chamber wall,
       said chamber wall having a reservoir portion,
       said high viscosity polymerizable dental composition being sealed within a cartridge chamber enclosed by said reservoir portion and said piston sealing wall, when said piston sealing wall is in sealing position,
       said reservoir portion having a cylindrical section and a hemispherical end, said hemispherical end being integrally connected to and opening into said discharge nozzle, said cylindrical section having a reservoir axis, said discharge nozzle having a nozzle axis, said nozzle axis intersects said reservoir axis at an angular offset,
       said reservoir portion having a reservoir length,
       said reservoir length being at least two times longer than said groove length,
    moving said piston sealing wall toward said groove inner end while passing a substantial portion of air through said groove channel,
    conveying said high viscosity polymerizable dental composition into said reservoir portion until said piston sealing wall is in sealing position and said cartridge chamber is effectively filled with at least 90 percent by volume of said high viscosity polymerizable dental composition and at most 10 percent by volume of air, and
    dispensing said high viscosity polymerizable dental composition from said reservoir portion onto a dental tooth.

13. The method of claim 12 wherein said dental cartridge further comprises a needle cannula, said needle cannula being connected to said discharge nozzle.

* * * * *